United States Patent [19]
Follettie et al.

[11] Patent Number: 5,935,852
[45] Date of Patent: Aug. 10, 1999

[54] DNA MOLECULES ENCODING MAMMALIAN CERBERUS-LIKE PROTEINS

[75] Inventors: Maximillian Follettie, Belmont, Mass.; Edward M. DeRobertis, Pacific Palisades, Calif.

[73] Assignee: Genetics Institute, Inc., Cambridge, Mass.

[21] Appl. No.: 08/887,997

[22] Filed: Jul. 3, 1997

[51] Int. Cl.[6] .......................... C12N 15/11; C12N 15/85; C12N 1/21; C07H 21/04

[52] U.S. Cl. ................. 435/325; 435/252.3; 435/252.33; 435/254.11; 435/320.1; 435/357; 435/358; 435/366; 536/23.1; 536/23.5; 536/24.31

[58] Field of Search .............................. 435/6, 69.1, 70.1, 435/71.1, 71.2, 91.1, 91.4, 325, 357, 358, 366, 252.3, 252.33, 254.11, 320.1; 514/44; 536/23.1, 23.5, 24.31, 24.33, 24.5, 25.3; 530/300, 350

[56] References Cited

U.S. PATENT DOCUMENTS 5,166,322  11/1992  Shaw et al. .

OTHER PUBLICATIONS

Bouwmeester et al., Nature 382:595–601 (1996).

Jung et al., J. Virol 63:1651–1660 (1989).

Ang et al., Cell 78:561–574 (1994).

Burgess et al, The Journal of Cell Biology, III:2129–2138, 1990.

Rudinger et al, in Peptide Hormones, Parsons et al eds, University Park Press, Jun. 1976 pp. 1–6.

Lazar et al, Molecular and Cellular Biology 8(3):1247–1252, 1998.

EST Accession Number AA 120122, GenBank, Nov. 19, 1996.

EST Accession Number AA 432482; GenBank ,May 22,1997.

*Primary Examiner*—Patricia Duffy
*Attorney, Agent, or Firm*—Steven R. Lazar

[57] ABSTRACT

DNA molecules are disclosed which encode mammalian Cerberus-Like Proteins.

16 Claims, No Drawings

DNA MOLECULES ENCODING MAMMALIAN CERBERUS-LIKE PROTEINS

The present invention relates to novel members of the cerberus protein family, DNA encoding them, and processes for obtaining them. These proteins may be used to induce expression of factors in and/or differentiation of tissue and organs, and particularly, inducing formation, growth, differentiation, proliferation and/or maintenance of neural, endoderm and cardiac tissue. Thus, these proteins may be useful in the treatment of wounds, tumors, and in the enhancement and/or inhibition of cellular formation, growth, differentiation, proliferation and/or maintenance of other tissue and organs, for example, epidermal, pancreatic, liver, spleen, lung, kidney, brain and/or other tissue. These proteins may also be used for augmenting the activity of other tissue regenerating and differentiation factors, such as the BMPs. The protein has been named mammalian cerberus-like by the inventors.

BACKGROUND OF THE INVENTION

The search for the molecule or molecules responsible for the formation, proliferation, differentiation and maintenance of tissue and organs, such as neurons and related neuronal cells and tissues, has been extensive as there is a tremendous need for factors useful for treating conditions involving degradation or damage to these tissues. A Xenopus protein previously identified in embryos, cerberus, appears to be involved in induction of the head. Bouwmeester et al., *Nature*, 382:595–601 (1996).

SUMMARY OF THE INVENTION

The inventors herein have discovered novel mammalian members of the cerberus family of proteins and have surprisingly discovered that members of the cerberus protein family are able to induce, enhance and/or inhibit the formation, growth, proliferation, differentiation, maintenance of neurons and/or related neural cells and tissues such as Schwann cells, glial cells and astrocytes. Accordingly, the present invention provides methods for inducing formation of neurons and/or related neural cells and tissues such as Schwann cells, glial cells and astrocytes, comprising administering to progenitor cells a composition comprising at least one protein which is a member of the cerberus protein family.

The present invention relates to a family of proteins designated as cerberus, which appears to be a pioneer protein, with a 9 cysteine residue pattern, which is present in the embryo. In *Xenopus*, cerberus mRNA is expressed at low levels in the unfertilized egg, and zygotic transcripts start accumulating at early gastrula. Expression continues during gastrulation and early neurulation, rapidly declining during neurulation. Importantly, cerberus expression starts about one hour after that of chordin, suggesting that cerberus could act downstream of the chordin signal. The cerberus domain of the organizer includes the leading edge of the most anterior organizer cells and extends into the lateral mesoderm. The leading edge gives rise to liver, pancreas and foregut in its midline, and the more lateral region gives rise to heart mesoderm at later stages of development.

In preferred embodiments, the composition may comprise a protein having the amino acid sequence of SEQUENCE ID NO:2 from amino acid 1, 18 to 24, 41, 85 to 91 or 162 to 241 or 272. In one embodiment, the method comprises administering the composition to a patient in vivo. Alternatively, the method may comprise administering the composition to cells in vitro and recovering neurons and/or related neural cells and tissues such as Schwann cells, glial cells and astrocytes, which may subsequently be administered to a patient. The composition may further comprise a suitable carrier for administration.

The present invention also provides novel DNA sequences encoding novel members of the cerberus protein family. In particular embodiments, the present invention provides novel DNA sequences encoding mammalian cerberus proteins such as murine and human cerberus. The nucleotide sequences, and the corresponding amino acid sequences encoded by these DNA sequences, are provided in the Sequence Listings. In particular, the present invention comprises isolated DNA sequence encoding a mammalian cerberus protein comprising a DNA sequence selected from the group consisting of: nucleotides #58, 109, 178, 313, 316, 319, 322, 325, 328, or 541 to #780 or 873 of SEQ ID NO: 1; or nucleotides encoding amino acids #1, 18, 41, 85 to 91 or 162 to #241 or 272 of SEQ ID NO: 2, as well as fragments and variants of the above sequences which are readily obtainable from the above and which maintain cerberus activity. The present invention further comprises sequences which hybridize to these sequences under stringent hybridization conditions and encode a protein which exhibits cerberus activity.

It is expected that mammalian cerberus protein, as expressed by mammalian cells such as CHO cells, exists as a heterogeneous population of active species of cerberus protein with varying N-termini. Based in part upon the Von Heginje signal peptide prediction algorithm, the first 17 to 24 amino acids appear to be involved in signaling for the secretion of the mature peptide. It is expected that active species may optionally include the signal peptide and will include amino acid sequences beginning with amino acid residues #1, 18, 19, 20, 21, 22, 23, 24 or 25 of SEQ ID NO:2. Thus, it is expected that DNA sequences encoding active mammalian cerberus proteins include those comprising nucleotides #109, 112, 115, 118, 121, 124, 127, 130 to #780 or 873 of SEQ ID NO: 1. Accordingly, active species of cerberus-like protein are expected to include those comprising amino acids #1, 18, 19, 20, 21, 22, 23, 24 or 25 to #241 or 272 of SEQ ID NO:2.

As described further herein, it is further expected that cerberus and cerberus-like proteins may be proteolytically processed by cells to form further active species. For example, putative proteolytic processing sites for cleavage, which are typically characterized by the formula R-X-K/R-R, are found at amino acids 37 to 40 and 82 to 85 of SEQ ID NO: 2. Thus, it is expected that DNA sequences encoding active mammalian cerberus proteins include those comprising nucleotides #178 or 313 to #780 or 873 of SEQ ID NO: 1. Accordingly, further active species of cerberus-like protein are expected to include those comprising amino acids #41 or 86 to #241 or 272 of SEQ ID NO: 2

In yet another embodiment, the present invention comprises a method of altering the regulation of genes in a patient in need of same comprising administering to said patient an effective amount of the above compositions. The alteration of regulation of neuronal genes may be accomplished by stimulating or inhibiting binding by cerberus proteins of receptor proteins. Thus, the mammalian cerberus and cerberus-like protein family may be capable of inducing formation of neural tissue.

In other embodiments, the present invention comprises vectors comprising the above DNA molecules in operative association with an expression control sequence therefor, as well as host cells transformed with these vectors. In yet other embodiments, the present invention comprises methods for producing purified mammalian cerberus proteins, novel mammalian cerberus proteins, and compositions containing the mammalian cerberus proteins. These methods may comprise the steps of: culturing a host cell transformed with a DNA sequence encoding a mammalian cerberus protein such as described above; and recovering and purifying said mammalian cerberus protein from the culture medium. The present invention further comprises the purified mammalian cerberus polypeptide produced by the above methods, as well as purified mammalian cerberus polypeptides comprising an amino acid sequence encoded by the above DNA sequences. The proteins of the present invention may comprise the amino acid sequence from amino acid #1, 18, 19, 20, 21, 22, 23, 24, 86, 87, 88, 89, 90, 91 or 162 to #241 or 272 of SEQ ID NO:2; or a mammalian cerberus protein having a molecular weight of about 20–30 kd, said protein comprising the amino acid sequence of SEQ ID NO: 2 and having the ability to regulate the transcription of one or more genes. One species of active cerberus-like protein is a mature peptide contemplated to comprise the amino acid sequence from amino acids 18 to 272 of SEQ ID NO:2 and have a molecular weight of about 28.6 kD. Another species of active cerberus-like protein is a cleaved peptide contemplated to comprise the amino acid sequence from amino acids 86 to 91 to 272 of SEQ ID NO:2, particularly from 90 to 272, and to have a molecular weight of about 20.7 kD.

Description of Sequences

SEQ ID NO: 1 nucleotide sequence of mammalian cerberus DNA, particularly murine cerberus DNA SEQ ID NO: 2 amino acid sequence of the mammalian cerberus protein encoded by SEQ ID NO: 1.

SEQ ID NO: 3 to 5 are consensus nucleotide sequences of probes to the cerberus and cerberus-like proteins.

SEQ ID NO:6 contains the recognition site for the restriction endonuclease XhoI.

SEQ ID NO:7 is a sequence including an XhoI recognition site.

SEQ ID NO:8 is a portion of the EMC virus leader sequence.

Description of ATCC Deposits

An *E. coli* DH5α strain transformed with pGIMCerb, which comprises the mammalian cerberus coding sequence described in Sequence ID NO: 1 has been deposited with the American Type Culture Collection, 12301 Parklawn Drive, Rockville, Md. 20852, and has been accorded the ATCC accession number 98347.

DETAILED DESCRIPTION OF THE INVENTION

As used herein, the terms "cerberus" or "cerberus-like" are both used to signify the protein family which comprises the cerberus and cerberus-like proteins. "cerberus or cerberus-like protein" refers to mammalian cerberus and cerberus-like proteins, such as the murine or human cerberus proteins, and other proteins which share sequence homology to the highly conserved cysteine pattern of the C-terminal portion of the mammalian cerberus proteins. One specific member of the cerberus protein family is the murine cerberus-like protein, having the amino acid sequence specified in SEQUENCE ID NO:2, as well as homologues of this protein found in other species; and other proteins which are closely related structurally and/or functionally to murine cerberus. It is also expected that cerberus related proteins also exist in other species, including family members in Xenopus, and Drosophila, *C. elegans*, zebrafish, as well as in all manmnals, for example, rats, mice and humans. "Cerberus or cerberus-like proteins" also includes variants of the cerberus proteins, such as allelic variants or variants induced by mutagenesis or deletions, and fragments of cerberus proteins which variants and fragments retain cerberus activity. "Cerberus and Cerberus-like" are also used to signify the family of proteins sharing structural and/or functional similarity, including those proteins which are described further herein.

As used herein, the term "cerberus or cerberus-like activity" refers to one or more of the activities which are exhibited by the mammalian cerberus-like proteins of the present invention. In particular, "cerberus or cerberus-like activity" includes the ability to induce, enhance and/or inhibit the formation, growth, proliferation, differentiation, maintenance of neurons and/or related neural cells and tissues such as brain cells, Schwann cells, glial cells and astrocytes. "Cerberus or cerberus-like" activity also includes the ability to induce molecular markers of neuroendocrine or ectoderm tissue, such as OTX2, N-CAM, MASH, chromagranin, and AP2, as well as the ability to induce the formation of neurons and/or related neural cells and tissues such as brain cells, Schwann cells, glial cells and astrocytes. "Cerberus or cerberus-like activity" may also include the ability to regulate the interaction of ligands and their protein receptors. "Cerberus or cerberus-like activity" may further include the ability to regulate the formation, differentiation, proliferation and/or maintenance of other cells and/or tissue, for example connective tissue, organs and wound healing. In particular, "cerberus or cerberus-like activity" may include the ability to enhance and/or inhibit the formation, growth, proliferation, differentiation and/or maintenance of cardiac, spleen, liver, pancreas, stomach, kidney, lung and brain cells and tissue, as well as osteoblasts and bone, chondrocytes and cartilage, tendon, epidermis and muscle. "Cerberus and cerberus-like activity" also includes the activities of cerberus and cerberus-like protein in the assays described in the examples and specification herein.

Cerberus and cerberus-like cDNA should be useful as a diagnostic tool (such as through use of antibodies in assays for proteins in cell lines or use of oligonucleotides as primers in a PCR test to amplify those with sequence similarities to the oligonucleotide primer, and to determine how much cerberus is present). Cerberus might act upon its target cells via its own receptor. Cerberus, therefore, may be useful for the isolation of that receptor. In addition, cerberus or its receptor should prove useful as a diagnostic probe for certain tumor types. Thus, cerberus, its receptor, or antibodies to either may be potent agonists or antagonists which may be clinically useful. In addition, complexes of cerberus and its receptor, cerberus and antibodies to it, or cerberus receptor and antibodies to it, may each be useful in a number of in vitro, ex vivo or clinical uses.

The present invention also includes protein variants and functional fragments of the amino acid sequence of the mammalian cerberus protein shown in SEQ ID NO: 2 which retain cerberus activity. The present invention also includes antibodies to a purified mammalian cerberus protein such as the above. The compositions of the present invention comprise a therapeutic amount of at least one of the above mammalian cerberus proteins. It is expected that such protein variants and functional fragments of cerberus or cerberus-like proteins will include amino acid sequences which share significant homology with the amino acid sequence of SEQ ID NO: 2, most preferably at least 80% or 90% amino acid identity. The variants and functional fragments which retain cerberus-like activity are expected to include those which retain the cysteine pattern found in the SEQ ID NO: 2. For example, a truncated polypeptide comprising amino acids #162 to #241 of SEQ ID NO: 2 will retain the full 9 cysteine pattern found in the carboxy terminal portion of the sequence of SEQ ID NO: 2.

In yet another embodiment, the present invention comprises a method of altering the regulation of genes in a patient in need of same comprising administering to said patient an effective amount of the above compositions. For example, the alteration of regulation of neuronal genes may be accomplished by stimulating or inhibiting binding of receptor proteins, for example, binding between the mammalian cerberus protein and its receptor protein. Thus, cerberus proteins may be capable of regulating the binding interaction of ligands to their receptor proteins, as well as the interaction of transcriptional factors on cells.

The present invention also encompasses hybrid or fusion vectors comprising the coding DNA sequences of the present invention and other cerberus encoding sequences, linked to a tissue specific or inducible regulatory sequence, such as a promoter or operator. In a preferred embodiment of the invention, the coding sequence for mammalian cerberus-like protein is operably linked to one or more promoters, enhancers and/or other regulatory elements from genes which are selectively expressed in neurons and/or related neural cells and tissues such as Schwann cells, glial cells and astrocytes. For example, the promoter of the GFAP gene, which is known to be expressed in astrocytes and neuronal cells; and the promoter of the OTX2 gene, which is known to be expressed in the anterior brain, are suitable for the tissue specific production of cerberus. Additionally, the DNA sequence encoding mammalian cerberus may be operatively linked to one or more regulatory sequences from GFAP or OTX2 proteins, as well as other proteins which are selectively produced in neurons and/or related neural cells and tissues such as Schwann cells, glial cells and astrocytes.

In other preferred embodiments of the invention, the coding sequence for mammalian cerberus-like protein is operably linked to the promoter isolated from other genes, organs or cells of interest. Vectors using other tissue-selective regulatory elements and inducible regulatory elements may also be useful for the selective or inducible expression of the mammalian cerberus-like proteins of the present invention.

Another aspect of the invention provides pharmaceutical compositions containing a therapeutically effective amount of mammalian cerberus-like protein, in a pharmaceutically acceptable vehicle or carrier. These compositions of the invention may be used in the formation of neurons and/or related neural cells and tissues such as Schwann cells, glial cells and astrocytes, as well as liver, pancreas, lung, heart, kidney, spleen, stomach, cardiac tissue and cells, as well as connective tissue and cells, including osteocytes, chondrocytes, myocytes, tendon cells, epidermal cells, and adipocytes. These compositions may further be utilized in order to enhance and/or inhibit the formation, growth, proliferation, differentiation and/or maintenance of bone, osteoblasts, cartilage, chondrocytes, beta cells and other cell types typically found in the islets of Langerhans or other pancreatic cells, as well as other organ tissues such as epidermis, spleen, brain, lung and kidney tissue. The compositions comprising mammalian cerberus-like protein may be used to treat precursor or stem cells, such as endoderm cells, which are able to differentiate into cells which comprise differentiated tissue or organs, such as cardiac and neural cells, in order to enhance the formation, differentiation, proliferation and/or maintenance of such cells, tissue or organs. Methods for forming and maintaining pancreatic cells are described, for example, in WO93/00441, the disclosure of which is hereby incorporated herein by reference. In addition, the compositions may be used to regulate embryonic development, for instance, by affecting the development of embryonic cells and tissue into the endodermal phenotype.

The compositions of the invention may comprise, in addition to a mammalian cerberus-like protein, other therapeutically useful agents including growth factors such as epidermal growth factor (EGF), fibroblast growth factor (FGF), transforming growth factor (TGF-α and TGF-β), Wnts, hedgehogs, including sonic, indian and desert hedgehogs, activins, inhibins, bone morphogenetic proteins (BMP), and insulin-like growth factor (IGF). The compositions may also include an appropriate matrix, for instance, for supporting the composition and providing a surface for ingrowth of neurons and/or related neural cells and tissues such as Schwann cells, glial cells and astrocytes, or for other tissue or cell growth. The matrix may provide slow release of the mammalian cerberus-like protein and/or the appropriate environment for presentation thereof.

The mammalian cerberus-like protein containing compositions may be employed in methods for treating a number of tissue defects, and healing and maintenance of various types of tissues and wounds. The tissues and wounds which may be treated include repair or induction of neurons and/or related neural cells and tissues such as Schwann cells, glial cells and astrocytes. It also includes treatment of cardiac, liver, pancreas, spleen, lung, kidney, brain and stomach tissue and may also include cartilage, epidermis, muscle, including cardiac muscle, other connective tissue, such as bone, tendon and ligament and other tissues and wounds. These methods, according to the invention, entail administering to a patient needing such tissue formation, wound healing or tissue repair, an effective amount of mammalian cerberus protein. The mammalian cerberus-like containing compositions may also be used to treat or prevent degenerative nerve conditions such as Parkinson's Disease, Alzheimer's Disease and Lou Gehrig's Disease, as well as other degenerative nerve diseases, and other conditions involving defects of neural tissue. The compositions may also be useful to treat other conditions such as osteoporosis, rheumatoid arthritis, osteoarthritis, and other abnormalities of connective tissue, or of other organs or tissues, such as muscle, pancreas, liver, spleen, lung, cardiac, brain, and kidney tissue, and other tissues and organs. These methods may also entail the administration of a protein of the invention in conjunction with administration of at least one other protein, for example growth factors including EGF, FGF, TGF-α, TGF-β, BMP, Wnts, hedgeghogs, including sonic, indian and desert hedgehogs, activin, inhibin and IGF. In a particular embodiment of the present invention the mammalian cerberus-like gene or protein may be used to augment the activities of BMPs or other members of the TGF-β superfamily.

Still a further aspect of the invention are DNA sequences coding for expression of mammalian cerberus-like protein. Such sequences include the sequence of nucleotides in a 5' to 3' direction illustrated in SEQ ID NO: 1, DNA sequences which, but for the degeneracy of the genetic code, are identical to the DNA sequence SEQ ID NO: 1, and encode the protein of SEQ ID NO: 2. Further included in the present invention are DNA sequences which hybridize under stringent conditions with the DNA sequence of SEQ ID NO: 1 and encode a protein having cerberus-like activity. Preferred DNA sequences include those which hybridize under stringent conditions [see, T. Maniatis et al, *Molecular Cloning (A Laboratory Manual)*, Cold Spring Harbor Laboratory (1982), pages 387 to 389]. It is generally preferred that such DNA sequences encode a polypeptide which is at least about 80% homologous, and more preferably at least about 90% homologous, to the mature mammalian cerberus-like amino acid sequence shown in SEQ ID NO:2. Further, allelic or other variations of the sequences of SEQ ID NO: 1, whether such nucleotide changes result in changes in the peptide sequence or not, but where the peptide sequence still has cerberus-like activity, are also included in the present invention. The present invention also includes functional fragments of the DNA sequence of mammalian cerberus-like proteins shown in SEQ ID NO: 1 which encode a polypeptide which retains the activity of cerberus-like protein. The determination whether a particular variant or fragment of the mammalian cerberus-like protein of the present invention, such as those shown in SEQ ID NO: 2 maintain cerberus-like activity, is routinely performed using the assays described in the examples and specification herein.

The DNA sequences of the present invention are useful, for example, as probes for the detection of mRNA encoding other cerberus-like proteins in a given cell population. The DNA sequences may also be useful for preparing vectors for gene therapy applications as described below.

A further aspect of the invention includes vectors comprising a DNA sequence as described above in operative association with an expression control sequence therefor. These vectors may be employed in a novel process for producing a recombinant mammalian cerberus-like protein of the invention in which a cell line transformed with a DNA sequence encoding mammalian cerberus-like protein in operative association with an expression control sequence therefor, is cultured in a suitable culture medium and mammalian cerberus-like protein is recovered and purified therefrom. This process may employ a number of known cells both prokaryotic and eukaryotic as host cells for expression of the polypeptide. The vectors may also be used in gene therapy applications. In such use, the vectors may be transfected into the cells of a patient ex vivo, and the cells may be reintroduced into a patient, or the vectors may be introduced into a patient in vivo through targeted transfection. Alternatively, native cerberus gene expression may be unregulated by known recombination techniques to insert high expression regulatory elements into the genome in proximity to the cerberus coding sequence disclosed herein.

In a preferred embodiment of the invention, vectors are prepared using one or more non-native regulatory elements, such as promoters and/or enhancers operatively associated with the coding sequence for mammalian cerberus-like, in order to achieve expression of mammalian cerberus-like in desired cell tissue and/or at a desired time in development. For example, a vector may be constructed using the promoter element from genes, which is known to be constitutively expressed in neuronal development. By operatively associating the promoter from suitable genes with the coding sequence for cerberus-like, and transforming suitable cells, such as neuronal stem cells, one can express mammalian cerberus-like in these cells, thus promoting the desired effects of formation, growth, proliferation, differentiation and/or maintenance of cells such as neurons and/or related neural cells and tissues such as Schwann cells, glial cells and astrocytes, either in in vitro culture or in vivo.

Still a further aspect of the invention are mammalian cerberus-like proteins or polypeptides. Such polypeptides are characterized by having an amino acid sequence including the sequence illustrated in SEQ ID NO: 2, variants of the amino acid sequence of SEQ ID NO: 2, including naturally occurring allelic variants, and other variants in which the protein retains cerberus-like activity, for example, the ability to enhance and/or inhibit the formation, growth, proliferation, differentiation and/or maintenance of neurons and/or related neural cells and tissues such as Schwann cells, glial cells and astrocytes, and may also affect the formation, growth, proliferation, differentiation and/or maintenance of pancreas, liver, stomach, cardiac, or other tissue such as bone, osteocytes, chondrocytes and/or cartilage tissue, or other organ tissue, such as spleen, lung, brain and kidney tissue, characteristic of cerberus-like protein. Preferred polypeptides include a polypeptide which is at least about 80% and more preferably at least about 90% homologous to the mature mammalian cerberus-like amino acid sequence shown in SEQ ID NO: 2. Further, allelic or other variations of the sequences of SEQ ID NO: 2, whether such amino acid changes are induced by mutagenesis, chemical alteration, or by alteration of DNA sequence used to produce the polypeptide, where the peptide sequence still has cerberus-like activity, are also included in the present invention. The present invention also includes fragments of the amino acid sequence of mammalian cerberus-like shown in SEQ ID NO:2 which retain the activity of cerberus-like protein. One skilled in the art can readily produce such variations and fragments of mammalian cerberus-like protein using techniques known in the art, and can readily assay them for activity, as described herein.

The purified proteins of the present inventions may be used to generate antibodies, either monoclonal or polyclonal, to mammalian cerberus-like proteins and/or other related proteins, using methods that are known in the art of antibody production. Thus, the present invention also includes antibodies to mammalian cerberus and/or other cerberus-like proteins. The antibodies may be useful for purification of mammalian cerberus-like proteins, or for inhibiting or preventing the effects of cerberus proteins either in vitro or in vivo. The mammalian cerberus-like proteins may be useful for inducing the growth and/or differentiation of embryonic cells and/or stem cells. Thus, the proteins or compositions of the present invention may also be useful for treating cell populations, such as embryonic cells or stem cell populations, to enhance, enrich or to inhibit the growth and/or differentiation of the cells. For example, the mammalian cerberus-like proteins may be useful for treating cell populations to enhance and/or inhibit the formation, differentiation, proliferation and/or maintenance of neurons and/or related neural cells and tissues such as Schwann cells, glial cells and astrocytes and/or other cells and tissue. The treated cell populations may be useful for, among other things, gene therapy applications, as described below. Thus, the proteins of the present invention may be useful in wound healing, tissue and organ repair and regeneration processes, as well as in differentiation of tissue, for example in embryonic development. In particular, it has been observed by the inventors that the mammalian cerberus-like protein may be useful for the induction, formation, growth, differentiation, proliferation and/or maintenance and repair of neurons and/or related neural cells and tissues such as Schwann cells, glial cells and astrocytes. The cerberus-like proteins are normally present as secreted proteins, and have been demonstrated to have effects on the growth and differentiation of neuronal and other neural cell and tissue types. Thus, these proteins, and compositions containing them, may be useful in the treatment of nerve and brain disorders, such as Parkinson's disease, Alzheimer's disease, and in the enhancement and/or inhibition of cellular formation, growth, differentiation, proliferation and/or maintenance, for example formation of neurons and/or related neural cells and tissues such as Schwann cells, glial cells and astrocytes.

The mammalian cerberus-like proteins provided herein include factors encoded by the sequences similar to those of SEQ ID NO:1, but into which modifications or deletions are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO:2. These sequences, by virtue of sharing primary, secondary, or tertiary structural and conformational characteristics with mammalian cerberus-like polypeptides of SEQ ID NO: 2 may possess biological properties in common therewith. Thus, these modifications and deletions of the native mammalian cerberus-like may be employed as biologically active substitutes for naturally-occurring mammalian cerberus-like polypeptides in therapeutic processes. It can be readily determined whether a given variant or fragment of mammalian cerberus-like protein maintains the biological activity of cerberus by subjecting both mammalian cerberus-like and the variant or fragment of mammalian cerberus-like to the assays described herein.

Other specific mutations of the sequences of mammalian cerberus-like proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Such variants of mammalian cerberus-like are within the present invention. Additionally, bacterial expression of mammalian cerberus-like proteins will result in production of a non-glycosylated protein, even if the glycosylation sites are left unmodified. Such bacterially produced versions of mammalian cerberus-like are within the present invention.

The present invention also encompasses the novel DNA sequences, free of association with DNA sequences encoding other proteinaceous materials, and coding for expression of mammalian cerberus-like proteins. These DNA sequences include those depicted in SEQ ID NO: 1 in a 5' to 3' direction and those sequences which hybridize thereto under stringent hybridization conditions [for example, 0.1 X SSC, 0.1% SDS at 65° C.; see, T. Maniatis et al, *Molecular Cloning* (*A Laboratory Manual*), Cold Spring Harbor Laboratory (1982), pages 387 to 389] and encode a protein having cerberus-like activity. Stringent hybridization conditions also refer to initial low stringency hybridization conditions, followed by higher stringency wash conditions. These DNA sequences also include those which comprise variants and fragments of the DNA sequence of SEQ ID NO: 1 which hybridize thereto under stringent hybridization conditions and encode a protein having cerberus-like activity.

Similarly, DNA sequences which code for mammalian cerberus-like proteins coded for by the sequences of SEQ ID NO: 1, or mammalian cerberus-like proteins which comprise the amino acid sequence of SEQ ID NO: 2, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO: 1 which are caused by point mutations or by induced modifications (including insertion, deletion, and substitution) to enhance the activity, half-life or production of the polypeptides encoded are also encompassed in the invention.

Another aspect of the present invention provides a novel method for producing mammalian cerberus-like proteins. The method of the present invention involves culturing a suitable cell line, which has been transformed with a DNA sequence encoding a mammalian cerberus-like protein of the invention, under the control of known regulatory sequences. The transformed host cells are cultured and the mammalian cerberus-like proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature*, 293:620–625 (1981), or alternatively, Kaufman et al, *Mol. Cell. Biol.*, 5(7): 1750–1759 (1985) or Howley et al, U.S. Pat. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method. For expression of the protein in bacterial cells, DNA encoding the propeptide of cerberus-like is generally not necessary.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these novel mammalian cerberus-like polypeptides. Preferably the vectors contain the full novel DNA sequences described above which encode the novel factors of the invention. Additionally, the vectors contain appropriate expression control sequences permitting expression of the cerberus-like protein sequences. Alternatively, vectors incorporating modified sequences as described above are also embodiments of the present invention. Additionally, the sequence of SEQ ID NO: 1 or other sequences encoding mammalian cerberus-like proteins could be manipulated to express a mature mammalian cerberus-like protein by deleting mammalian cerberus-like propeptide sequences and replacing them with sequences encoding the complete propeptides of other cerberus-like proteins or other suitable propeptides. Thus, the present invention includes chimeric DNA molecules encoding a propeptide from a member of the cerberus-like family linked in correct reading frame to a DNA sequence encoding a mammalian cerberus-like polypeptide.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

In order to produce rat, human or other mammalian cerberus-like proteins, the DNA encoding it is transferred into an appropriate expression vector and introduced into mammalian cells or other preferred eukaryotic or prokaryotic hosts by conventional genetic engineering techniques. The preferred expression system for biologically active recombinant mammalian cerberus-like is contemplated to be stably transformed mammalian cells.

One skilled in the art can construct mammalian expression vectors by employing the sequence of SEQ ID NO: 1, or other DNA sequences encoding cerberus-like proteins or other modified sequences and known vectors, such as pCD [Okayama et al., *Mol. Cell Biol.*, 2:161–170 (1982)], pJL3, pJL4 [Gough et al., *EMBO J.*, 4:645–653 (1985)] and pMT2 CXM.

```
CTGCAGGCGAGCCTGAATTCCTCGAGCCATCATG-3'        (SEQ ID NO:7)
         PstI       Eco RI XhoI
```

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufmnan, R. J., 1985, Proc. Natl. Acad. Sci. USA 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM is obtained by EcoRI digestion of pMT2-VWF, which has been deposited with the American

```
5'CGAGGTTAAAAAACGTCTAGGCCCCCCGAACCACGGGGACGTGGTTT    (SEQ ID NO:8)

TCCTTT
 TaqI

GAAAAACACGATTGC-3'
      XhoI
```

Type Culture Collection (ATCC), Rockville, Md. (USA) under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods. pMT2 CXM is then constructed using loopout/in mutagenesis [Morinaga, et al., *Biotechnology* 84: 636 (1984). This removes bases 1075 to 1145 relative to the Hind III site near the SV40 origin of replication and enhancer sequences of pMT2. In addition it inserts the following sequence:

5'PO-CATGGGCAGCTCGAG-3' (SEQ ID NO: 6)

at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform *E. Coli* HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR: 5'-

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B 1.

A portion of the EMCV leader is obtained from pMT2-ECAT1 [S. K. Jung, et al, *J. Virol* 63:1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

This sequence matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1. This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the mammalian cerberus DNA sequences. For instance, mammalian cerberus cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of mammalian cerberus proteins. Additionally, the sequence of SEQ ID NO: 1 other sequences encoding mammalian cerberus proteins can be manipulated to express a mature mammalian cerberus protein by deleting mammalian cerberus encoding propeptide sequences and replacing them with sequences encoding the complete propeptides of other proteins.

One skilled in the art can manipulate the sequences of SEQ ID NO: 1 by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences therefrom or altering nucleotides therein by other known techniques). The modified mammalian cerberus coding sequence could then be inserted into a known bacterial vector using procedures such as described in T. Taniguchi et al., *Proc. Natl Acad. Sci. USA*, 77:5230–5233 (1980). This exemplary bacterial vector could then be transformed into bacterial host cells and a protein expressed thereby. For a strategy for producing extracellular expression of mammalian cerberus proteins in bacterial cells, see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a mammalian cerberus protein of the invention in mammalian cells may involve the construction of cells containing multiple copies of the heterologous mammalian cerberus gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For example, a plasmid containing a DNA sequence for a mammalian cerberus protein of the invention in operative association with other plasmid sequences enabling expression thereof and the DHFR expression plasmid pAdA26SV (A)3 [Kaufman and Sharp, *Mol. Cell. Biol.*, 2:1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5uM MTX) as described in Kaufman et al., *Mol Cell Biol.*, 5:1750 (1983). Transformants are cloned, and biologically active mammalian cerberus expression is monitored by assay in one of the assays described in the examples and specification. Mammalian cerberus protein expression should increase with increasing levels of MTX resistance. Mammalian cerberus polypeptides are characterized using standard techniques known in the art such as pulse labeling with [35S] methionine or cysteine and polyacrylamide gel electrophoresis. Similar procedures can be followed to produce other related cerberus proteins.

A mammalian cerberus protein of the present invention, which demonstrates cerberus activity, has application in the induction, formation, growth, differentiation, proliferation and/or maintenance and healing of cells and tissues such as neurons and/or related neural cells and tissues such as Schwann cells, glial cells and astrocytes, and other tissues, in humans and other animals. Such a preparation employing mammalian cerberus protein may have prophylactic use in treatment of Parkinson's disease, Alzheimer's disease, as well as preventing neural tumors, and other neural tissue disorders. De novo formation of neurons and/or related neural cells and tissues such as Schwann cells, glial cells and astrocytes, and other cells of neural phenotype, induced by a cerberus protein contributes to the repair of congenital, trauma induced, or oncologic tissue defects or conditions. Mammalian cerberus protein may also be used in the treatment of neural disease, and in other tissue and organ repair processes. Such agents may provide an environment to attract suitable stem cells, stimulate growth and proliferation of neuron-forming cells or induce differentiation of progenitors of neuron-forming cells, and may also support the regeneration of other tissues and organs. Mammalian cerberus polypeptides of the invention may also be useful in the treatment of organ disorders.

The proteins of the invention may also be used in wound healing and in related tissue repair. The types of wounds include, but are not limited to burns, incisions and ulcers. (See, e.g. PCT Publication WO84/01106 for discussion of wound healing and related tissue repair). It is further contemplated that proteins of the invention may increase neuronal, astrocytic and/or glial cell survival and therefore be useful in transplantation and treatment of conditions exhibiting a decrease in neuronal survival and repair. The proteins of the invention may further be useful for the treatment of conditions related to other types of tissue, such as epidermis, muscle, connective tissue, such as bone, cartilage, tendon and ligament, and other organs such as pancreas, liver, spleen, lung, cardiac, brain and kidney tissue. The proteins of the present invention may also have value as a dietary supplement, or as additives for cell culture media. For this use, the proteins may be used in intact form, or may be predigested to provide a more readily absorbed supplement.

The proteins of the invention may also have other useful properties characteristic of the cerberus family of proteins. Such properties include angiogenic, chemotactic and/or chemoattractant properties, and effects on cells including differentiation responses, cell proliferative responses and responses involving cell adhesion, migration and extracellular matrices. These properties make the proteins of the invention potential agents for wound healing, reduction of fibrosis and reduction of scar tissue formation. The proteins of the invention may also be useful for the induction of formation of cells capable of secreting valuable hormones, including endocrine or exocrine hormones.

A further aspect of the invention is a therapeutic method and composition for treating disorders of neurons and/or related neural cells and tissues such as Schwann cells, glial cells and astrocytes, and other conditions related to neuronal and neural tissue disorders or diseases. The invention further comprises therapeutic methods and compositions for wound healing and tissue repair. Such compositions comprise a therapeutically effective amount of at least one mammalian cerberus protein of the present invention in admixture with a pharmaceutically acceptable vehicle, carrier or matrix. It is further contemplated that compositions of the invention may increase neuronal, glial cell and astrocyte survival and therefore be useful in transplantation and treatment of conditions exhibiting a decrease in neuronal survival.

It is expected that cerberus and cerberus-like proteins may exist in nature as homodimers or heterodimers. To promote the formation of dimers of cerberus-like protein with increased stability, one can genetically engineer the DNA sequence of SEQUENCE ID NO: 1 to provide one or more additional cysteine residues to increase potential dimer formation. The resulting DNA sequence would be capable of producing a "cysteine added variant" of cerberus-like protein. Alternatively, one can produce "cysteine added variants" of cerberus-like proteins by altering the sequence of the protein at the amino acid level, for example, by altering the amino acid sequences of one or more amino acid residues to Cys. Production of "cysteine added variants" of proteins is described in U.S. Pat. No. 5,166,322, the disclosure of which is hereby incorporated by reference.

It is expected that the proteins of the invention may act in concert with or perhaps synergistically with other related proteins and growth factors. Such combinations may comprise separate molecules of the cerberus or cerberus-like proteins and other proteins or heteromolecules comprised of different moieties. For example, a method and composition of the invention may comprise a disulfide linked dimer comprising a cerberus protein subunit and a subunit from one of the "BMP" proteins. Thus, the present invention includes a purified cerberus-like polypeptide which is a heterodimer wherein one subunit comprises an amino acid sequence of SEQ ID NO:2, and one subunit comprises an amino acid sequence for a bone morphogenetic protein selected from the group consisting of BMP-2, BMP-3, BMP4, BMP-5, BMP-6, BMP-7, BMP-8, BMP-9, BMP-10, BMP-11, BMP-12 or BMP-13, disclosed in PCT application WO 95/16035, or BMP-15, disclosed in PCT application WO96/36710 or BMP-16, disclosed in co-pending patent application Ser. No. 08/715,202, filed Sep. 18, 1996. A further embodiment may comprise a heterodimer of cerberus moieties, for example, of *Xenopus cerberus* and a mammalian homologue of *Xenopus cerberus* or other cerberus-like protein. Further therapeutic methods and compositions of the invention therefore comprise a therapeutic amount of at least one mammalian cerberus protein of the invention with a therapeutic amount of at least one other protein, such as a member of the TGF-β superfamily of proteins, which includes the bone morphogenetic proteins (BMPs), growth and differentiation factors (GDFs) and other proteins. The composition may include other agents and growth factors such as epidermal growth factor (EGF), fibroblast growth factor (FGF), platelet derived growth factor (PDGF), transforming growth factors (TGF-α and TGF-β), Wnts, hedgeghogs, including sonic, indian and desert hedgehogs, activins, inhibins, and k-fibroblast growth factor (kFGF), parathyroid hormone (PTH), leukemia inhibitory factor (LIF/HLDA/DIA), insulin-like growth factors (IGF-I and IGF-II). Portions of these agents may also be used in compositions of the present invention.

The preparation and formulation of such physiologically acceptable protein compositions, having due regard to pH, isotonicity, stability and the like, is within the skill of the art. The therapeutic compositions are also presently valuable for veterinary applications due to the lack of species specificity in cerberus proteins. Particularly domestic animals and thoroughbred horses in addition to humans are desired patients for such treatment with the cerberus proteins of the present invention.

The therapeutic method includes administering the composition topically, systemically, or locally as by injection or implantation. When administered, the therapeutic composition for use in this invention is, of course, in a pyrogen-free, physiologically acceptable form. Further, the composition may desirably be encapsulated or injected in a viscous form for delivery to the site of neurons and/or related neural cells and tissues such as Schwann cells, glial cells and astrocytes or other tissue damage. Topical administration may be suitable for wound healing and tissue repair. Therapeutically useful agents other than the cerberus proteins which may also optionally be included in the composition as described above, may alternatively or additionally, be administered simultaneously or sequentially with the cerberus composition in the methods of the invention.

For implantation, the composition preferably includes a matrix capable of delivering mammalian cerberus proteins to the site of neurons and/or related neural cells and tissues such as Schwann cells, glial cells and astrocytes or other tissue damage, providing a structure for the developing tissue and optimally capable of being resorbed into the body. The matrix may provide slow release of mammalian cerberus and/or other protein, as well as proper presentation and appropriate environment for cellular infiltration. Such matrices may be formed of materials presently in use for other implanted medical applications. The choice of matrix material is based on biocompatibility, biodegradability, mechanical properties, cosmetic appearance and interface properties. The particular application of the mammalian cerberus compositions will define the appropriate formulation.

The dosage regimen will be determined by the attending physician considering various factors which modify the action of the mammalian cerberus protein, e.g. amount of tissue desired to be formed, the site of tissue damage, the condition of the damaged tissue, the size of a wound, type of damaged tissue, the patient's age, sex, and diet, the severity of any infection, time of administration and other clinical factors. The dosage may vary with the type of matrix used in the reconstitution and the types of mammalian cerberus proteins in the composition. The addition of other known growth factors, such as IGF I (insulin like growth factor I), to the final composition, may also effect the dosage.

Progress can be monitored by periodic assessment of tissue growth and/or repair. The progress can be monitored, for example, x-rays, histomorphometric determinations and tetracycline labeling.

The following examples illustrate practice of the present invention in recovering and characterizing mammalian cerberus protein and employing the DNA to recover other cerberus proteins, obtaining the human proteins and expressing the proteins via recombinant techniques. As will be recognized, numerous variations of the materials and methods described can be prepared and are within the invention.

EXAMPLE 1
Cloning of a Murine Homologue to *Xenopus cerberus*

The carboxy-terminal, cysteine rich domain of xenopus cerberus was used to screen mammalian libraries and ESTS reported in GENBANK. An EST, AA120122, derived from the Beddington day 7.5 embryonic region library was identified by sequence homology to xenopus cerberus. While the partial clone has almost no sequence conservation in the N-terminal half of the molecule, the C-terminal domain and especially the pattern of the nine cysteines showed sequence conservation. The full-length cDNA encoding the murine cerberus-like protein was isolated from a murine embryonic cell cDNA library and the gene isolated from a murine genomic library.

Murine cerberus-like cDNA (SEQ ID NO: 1) encodes a 272 amino acid protein with predicted MW 30.5 Kd (SEQUENCE ID NO:2). The murine cerberus-like gene, Mcerb-1, has a single 2 Kb intron at position 564 of the cDNA SEQ ID NO: 1. The predicted protein contains a hydrophobic signal sequence at its amino terminus, indicating the molecule is secreted. Analysis by Sigcleave indicates that the first 17 resides are cleaved from the mature molecule upon secretion (Sigcleave score=7.6). The mature murine cerberus-like protein is predicted to be a 255 residue protein of MW 28.6 Kd including residues 18–272 of SEQ ID NO:2. The cerberus-like cDNA was expressed in COS cells and labeled with $^{35}$S-Met/$^{35}$S-Cys. The resulting protein was secreted into the culture medium and resulted in a smeared band of MW 38–44 Kd when fractionated on 16% polyacrylamide reducing gels. The smeared bands indicate that the protein is glycosylated consistent with the two putative N-linked glycosylation sites in the sequence. Expression of the protein in reticulocyte systems shows a 33 kD band consistent with predicted protein in the absence of glycosylation. When fractionated on non-reducing polyacrylamide gels, approximately half of the COS expressed material runs with a molecular weight of 78–84 Kd indicating the protein is capable of forming cysteine-linked homodimers. The protein sequence contains a hydrophobic signal sequence at its amino terminus and a cysteine-rich domain close to its carboxy terminus. The cysteine-rich domains of *Xenopus cerberus* and murine cerberus-like proteins are 58% identical and the overall amino acids are 31 % identical. The nine cysteine pattern at the carboxy terminus is conserved between *Xenopus cerberus* and mammalian cerberus-like protein.

EXAMPLE 2

Mammalian cerberus-like Encodes a Secreted Protein

To test whether the full length cDNA encoded a secreted protein, the 293T human cell line was transiently transfected with the DNA sequence of SEQ ID NO: 1, which encodes mammalian cerberus-like protein, cloned in an eukaryotic expression vector and labelled with $^{35}$S-methionine. A broad band was secreted into the culture medium, as well as a minor form. Similar to the COS cell expression, fractionation of the material expressed in 293T cells evidenced the formation of cysteine-linked dimers. The cerberus-like protein is presumably glycosylated since the protein translated in the reticulocyte system (in the absence of membranes) results in a band of 33 kD molecular weight corresponding to the molecular weight predicted from the amino acid sequence. Cerberus-like protein has two putative N-linked glycosylation sites. Accordingly, the DNA of SEQ ID NO: 1 defines a secreted protein with high amino acid identity to *Xenopus cerberus* in the cysteine-rich domain.

EXAMPLE 3

Expression of Mammalian Cerberus-like Protein

In prestreak mouse embryos (5.5 days post coitum), mammalian cerberus-like transcripts were detected on one side of the primitive endoderm, including the distal tip of the embryo. At early primitive streak, expression was found in a patch of primitive endoderm cells on one side of the embryonic region and no longer extends to the tip of the embryo. This patch corresponded to the anterior side of the embryo, because in sections it is found in the endoderm opposite to the forming primitive streak which can be recognized as a thickening of the posterior epiblast. At mid-streak, the cerberus-like positive area remained in the anterior primitive endoderm. At the late streak stage, when the node has reached the distal tip of the embryo, a second population of cerberus-like expressing was seen in the region surrounding the node. These cells presumably correspond to definitive endodermal cells, that are known to emerge from the node. The endodermal nature of this cell population was confirmed by histological analysis. At the neural plate stage, cerberus-like is found underlying the anterior neural plate, in a pattern comparable to the domain of Otx2 expression in endoderm. Ang et al., *Cell*, 78:561–574 (1994). At this stage, the cerberus-like positive cell population presumably consists of both primitive and definitive endoderm, and do not include the node itself. Importantly, cells expressing the cerberus-like secreted factor are in direct contact with cells that subsequently give rise to the fore- and midbrain region of the CNS.

At the early headfold stage, cerberus-like signal in the endoderm stats to weaken. At late headfold, cerberus-like expression is confined to the midline and adjoining endoderm. Expression is found in all cells of the midline from the rostral end of the embryo to the proximity of the node and includes anterior gut endoderm and mesoderm from the prechordal and notochordal plates. Expression of cerberus-like mRNA in anterior endoderm remains until the start of somitogenesis and then becomes undetectable. Concomitantly, a late phase of expression begins in the mesoderm of the somites. Thus, cerberus-like defines an anterior domain of the endoderm in early mouse embryos. Expression is found in anterior endoderm in direct contact with the future neural plate, but never detected in posterior endoderm cells in contact with the primitive streak, providing further evidence in support of the role of cerberus-like in the induction of anterior neuroectoderm.

EXAMPLE 4

Assays to Determine Function of Cerberus or Cerberus-Like in the Mouse

To determine function of cerberus and cerberus-like genes in the mouse embryo, transgenic knockout and misexpression mice can be made by engineering of murine embryonic stem (ES) cells and injection into the blastula using standard procedures. The murine knockout can be achieved by replacing a central portion of the cerberus or cerberus like genes with a selectable marker (e.g., neo), transfecting the construct into ES cells and selecting for the double crossover. For misexpression, the cerberus and cerberus-like genes can be engineered to be expressed from generic (e.g., actin) or tissue specific (e.g., IDX) promoters and reintroduced into murine ES cells. Transgenic animals can be generated from such engineered cells using classical procedures.

To determine the function of the cerberus or cerberus like proteins in the adult mouse, the protein can be directly injected into tissues or delivered by viral vectors. For example, the cerberus or cerberus-like genes can be transiently overexpressed in the adult mouse using adenovirus vectors and the function or activity of the proteins investigated by physiological, histochemical and biochemical analysis of the animals.

EXAMPLE 5
Isolation of Human Cerberus and Cerberus-like Genes

Hybridization of the murine cerberus-like gene to human DNA sequences identified a single XbaI generated band of approximately 15 Kb demonstrating its utility as probe to identify the human cerberus-like gene within a human genomic library. Alignment of the *Xenopus cerberus* and murine cerberus-like genes has identified three regions of sufficient nucleic acid homology within the cysteine rich domain to serve as probes for the human cerberus and cerberus-like genes. The consensus sequences for the three probes are:

(1) TGCCCTTCAMYCAGAMYATTGYMCATGAARAC
    TGT    [SEQ ID NO:3];

(2) CAGAACAAYCTKTGCTTTGGTAAAT
    GCA    [SEQ ID NO:4];

and (3) TGYTCCCAYTGCTYGCCSWCCAAATT    [SEQ ID NO: 5].

The first probe spans the 2 Kb intron in the mouse gene and is therefore less likely to function well as a probe. Used individually or together, the latter two oligos containing 6-fold and 10-fold degeneracy, respectively, would serve as probes for human cerberus and cerberus-like genes in genomic or cDNA libraries.

EXAMPLE 6
Identification and Isolation of Additional Cerberus and Cerberus-like Proteins The cerberus and cerberus-like proteins are members of a family which can be recognized by their unique cysteine pattern. This family includes cerberus, cerberus-like protein, Dan protein and Norrie protein. Dan protein is a tumor suppressor candidate and defects in the Norrie protein result in congenital defects including blindness and deafness. Members of the cerberus family thus seem to play an important role in cell differentiation and proliferation and thus it is important to find other members of this family of proteins. Family members cannot necessarily be recognized by amino acid homology, which demonstrates a significant amount of diversity, but can be recognized by a unique pattern of nine cysteines. The consensus cysteine pattern in each of these proteins is: in immediate sequence, a first cysteine residue, 13–15 non-cysteine amino acid residues, a second cysteine, 9 non-cysteine amino acid residues, a third cysteine residue, 1 non-cysteine amino acid residue, 1 glycine residue, 1 non-cysteine amino acid residue, a fourth cysteine, 14–23 non-cysteine amino acid residues, a fifth cysteine amino acid residue, two non-cysteine amino acid residues, a sixth cysteine residue, 13 non-cysteine amino acid residues, a seventh cysteine residue, 15–18 non-cysteine amino acid residues, an eighth cysteine residue, 1 non-cysteine amino acid residue, and a ninth cysteine residue, found in the conserved cysteine pattern of the cerberus and cerberus-like families of proteins.

By searching mammalian ESTs for this motif, novel members of the cerberus family have been identified including the human EST N35377 and the murine EST AA289245. Using standard procedures, the full length genes can be isolated from either genomic or cDNA libraries. These genes are expected to encode signaling proteins which function to pattern the embryo, control cellular differentiation or cell proliferation and thus be candidate proteins in medical therapy.

Within the cysteine-rich domains of *Xenopus cerberus* and murine cerberus-like proteins are two discrete subregions which are highly conserved cysteine motifs and may be particularly useful for the identification and isolation of cerberus and cerberus-like proteins from other species, as well as related members of the cerberus and cerberus-like protein families. Use of these highly conserved motifs to screen mammalian libraries and ESTS reported in GEN-BANK is expected to identify additional proteins of the cerberus and cerberus-like families of proteins from humans and other species, as well as identify further family members may be found. The first region is the motif of a five amino acid sequence wherein the first amino acid residue is a cysteine, the second amino acid residue is a non-cysteine amino acid, the third amino acid residue is glycine, the fourth amino acid residue is a non-cysteine amino acid, the fifth amino acid residue is a cysteine which corresponds to Cys-Phe-Gly-Lys-Cys found at amino acid residues 186 to 190 of SEQ ID NO: 1. Thus, degenerate oligonucleotides to the sequence TGC TTT GGC AAA TGC at nucleotide positions 613 to 627 of SEQ ID NO: 1, and the adjoining regions, may be useful to identify and isolate other genes which share the five amino acid sequence motif, wherein the first amino acid residue is a cysteine, the second amino acid residue is a non-cysteine amino acid, the third amino acid residue is glycine, the fourth amino acid residue is a non-cysteine amino acid, the fifth amino acid residue is a cysteine, of cerberus and cerberus-like proteins. A second highly conserved region within the cysteine-rich domains of *Xenopus cerberus* and murine cerberus-like proteins is the motif of a four amino acid sequence wherein the first amino acid residue is a cysteine, the second and third amino acid residues are each a non-cysteine amino acid, and the fourth amino acid residue is a cysteine which corresponds to Cys-Ser-His-Cys found at amino acid residues 206 to 209 of SEQ ID NO: 1. Thus, degenerate oligonucleotides to the sequence TGC TTC CAC TGC at nucleotide positions 673 to 684 of SEQ ID NO: 1, and the adjoining regions, may be useful to identify and isolate other genes which share the four amino acid sequence motif, wherein the first amino acid residue is a cysteine, the second and third amino acid residues are each a non-cysteine amino acid, and the fourth amino acid residue is a cysteine, of cerberus and cerberus-like proteins. Using the above motifs, additional proteins of the cerberus and cerberus-like families of proteins may be identified from other species, and further family members from humans, mice or frogs may be found. Use of the two motifs above in concert may further provide specific identification and isolation of additional cerberus and cerberus-like family members.

EXAMPLE 7
Microinjection Assays for Cerberus and Cerberus-Like Activity

Injection of MRNA encoding xenopus cerberus into xenopus blastomeres at different stages (4 cell, 8 cell and 32 cell) has profound effects on the expression pattern of specific genes and on the resulting morphology of the developing embryo. Misexpression of cerberus inhibits development of the prechordal plate, notochord and ventral trunk mesoderm and their respective molecular markers, goosecoid, collagen II and x-globin. Microinjection of cerberus induces anterior neuroectodermal structures such as brain, olfactory placodes and cement gland. Cerberus induced gene expression includes N-CAM (brain), Otx2 (anterior brain), CG-13 (cement gland) and Nkx-2.5 (heart primordium). Induction of neural tissue by cerberus was specific to anterior region of the brain as indicated by upregulation of the Otx2 marker but not more posterior markers including En-2 (midbrain-hind brain junction), Krox-20 (hind brain) and X1Hbox-6 (spinal cord). Injection of cerberus into specific cells of the 32-cell blastomere resulted in the induction of ectopic heads, and duplicate heart and liver.

Like cerberus, microinjection of cerberus-like mRNA into animal cap explants induces anterior CNS in xenopus embryos. However, microinjection of mammalian cerberus-like mRNA into xenopus embryos did not induce formation of ectopic head structures, for example, containing forebrain, cyclopic eyes, olfactory placodes and cement glands, suggesting overlapping but not identical functional effects. Thus, cerberus-like is a neuralizing factor, that leads to the formation of forebrain in xenopus assays.

EXAMPLE 8
Additional Embryonic Stem Cell Assay

In order to assay the effects of the cerberus-like proteins of the present invention, it is possible to assay the growth and differentiation effects in vitro on a number of available embryonic stem cell lines. One such cell line is ES-E14TG2, which is available from the American Type Culture Collection in Rockville, Md.

In order to conduct the assay, cells may be propagated in the presence of 100 units of LIF to keep them in an undifferentiated state. Assays are setup by first removing the LIF and aggregating the cells in suspension, in what is known as embryoid bodies. After 3 days the embryoid bodies are plated on gelatin coated plates (12 well plates for PCR analysis, 24 well plates for immunocytochemistry) and treated with the proteins to be assayed. Cells are supplied with nutrients and treated with the protein factor every 2–3 days. Cells may be adapted so that assays may be conducted in media supplemented with 15% Fetal Bovine Serum (FBS) or with CDM defined media containing much lower amounts of FBS.

At the end of the treatment period (ranging from 7–21 days) RNA is harvested from the cells and analyzed by quantitative multiplex PCR for the following markers: Brachyury, a mesodermal marker, AP-2, an ectodermal marker, and HNF-3α an endodermal marker. Through immunocytochemistry, it is also possible to detect the differentiation of neuronal cells (glia, astrocytes and neurons), muscle cells (cardiomyocytes, skeletal and smooth muscle), and various other phenotype markers such as proteoglycan core protein (cartilage), and cytokeratins (epidermis). Since these cells have a tendency to differentiate autonomously when LIF is removed, the results are always quantitated by comparison to an untreated control.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

All of the publications and patents referred to herein are hereby specifically incorporated by reference, as if fully set forth herein for the referred to disclosure.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 1003 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 58..873

(xi) SEQUENCE DESCRIPTION: SEQ ID NO:1:

GAATTCGGCC AAAGAGGCCT ATGTGAATCT AACCTCAGTC TCTGGGAATC AG
GAAGC          57

ATG CAT CTC CTC TTA GTT CAG CTG CTT GTT CT
C TTG CCT CTG GGG AAG          105
Met His Leu Leu Leu Val Gln Leu Leu Val Le
u Leu Pro Leu Gly Lys
    1               5
                        10
                        15

GCA GAC CTA TGT GTG GAT GGC TGC CAG AGT CA
G GGC TCT TTA TCC TTT          153
Ala Asp Leu Cys Val Asp Gly Cys Gln Ser Gl
n Gly Ser Leu Ser Phe

```
                 20
                 25
                 30

CCT CTC CTA GAA AGG GGT CGC AGA GAT CTC CA
C GTG GCC AAC CAC GAG         201
Pro Leu Leu Glu Arg Gly Arg Arg Asp Leu Hi
s Val Ala Asn His Glu
                 35
                 40
                 45

GAG GCA GAA GAC AAG CCG GAT CTG TTT GTG GC
C GTG CCA CAC CTC ATG         249
Glu Ala Glu Asp Lys Pro Asp Leu Phe Val Al
a Val Pro His Leu Met
                 50
                 55
                 60

GGC ACC AGC CTG GCT GGG GAA GGC CAG AGG CA
G AGA GGG AAG ATG CTG         297
Gly Thr Ser Leu Ala Gly Glu Gly Gln Arg Gl
n Arg Gly Lys Met Leu
 65
 70
 75
 80

TCC AGG CTT GGA AGA TTC TGG AAG AAA CCT GA
G ACC GAA TTT TAC CCC         345
Ser Arg Leu Gly Arg Phe Trp Lys Lys Pro Gl
u Thr Glu Phe Tyr Pro
                 85
                 90
                 95

CCA AGG GAT GTG GAA AGC GAT CAT GTC TCA TC
G GGG ATG CAG GCC GTG         393
Pro Arg Asp Val Glu Ser Asp His Val Ser Se
r Gly Met Gln Ala Val
                100
                105
                110

ACT CAG CCA GCA GAT GGG AGG AAA GTG GAG AG
A TCA CCT CTA CAG GAG         441
Thr Gln Pro Ala Asp Gly Arg Lys Val Glu Ar
g Ser Pro Leu Gln Glu
                115
                120
                125

GAA GCC AAG AGG TTC TGG CAT CGG TTC ATG TT
C AGA AAG GGC CCG GCG         489
Glu Ala Lys Arg Phe Trp His Arg Phe Met Ph
e Arg Lys Gly Pro Ala
                130
                135
                140

TTC CAG GGA GTC ATC CTG CCC ATC AAA AGC CA
C GAA GTA CAC TGG GAG         537
Phe Gln Gly Val Ile Leu Pro Ile Lys Ser Hi
s Glu Val His Trp Glu
145                              1
50                               1
55                               1
60

ACC TGC AGG ACT GTG CCC TTC AAC CAG ACC AT
T GCC CAT GAA GAC TGT         585
Thr Cys Arg Thr Val Pro Phe Asn Gln Thr Il
e Ala His Glu Asp Cys
                165
                170
                175

CAA AAA GTC GTT GTC CAG AAC AAC CTT TGC TT
T GGC AAA TGC AGT TCC         633
```

```
Gln Lys Val Val Gln Asn Asn Leu Cys Ph
e Gly Lys Cys Ser Ser
            180
                185
                    190

ATT CGT TTT CCC GGA GAA GGG GCA GAT GCC CA
C AGC TTC TGC TCC CAC        681
Ile Arg Phe Pro Gly Glu Gly Ala Asp Ala Hi
s Ser Phe Cys Ser His
        195
            200
                205

TGC TCG CCC ACC AAA TTC ACC ACC GTG CAC TT
G AGG CTG AAC TGC ACC        729
Cys Ser Pro Thr Lys Phe Thr Thr Val His Le
u Arg Leu Asn Cys Thr
      210
          215
              220

AGC CCA ACC CCC GTG GTC AAG ATG GTG ATG CA
A GTA GAA GAG TGT CAG        777
Ser Pro Thr Pro Val Val Lys Met Val Met Gl
n Val Glu Glu Cys Gln
225               2
30                 2
35                  2
40

TGC ATG GTG AAG ACG GAA CGT GGA GAG GAG CG
C CTC CTA CTG GCT GGT        825
Cys Met Val Lys Thr Glu Arg Gly Glu Glu Ar
g Leu Leu Leu Ala Gly
              245
                  250
                      255

TCC CAG GGT TCC TTC ATC CCT GGA CTT CCA GC
T TCA AAA ACA AAC CCA        873
Ser Gln Gly Ser Phe Ile Pro Gly Leu Pro Al
a Ser Lys Thr Asn Pro
            260
                265
                    270

TGATTACCTC AACAGAAAGC AAAACCTCAA CAGAATAAGT GAGGGTTATT CA
ATCTGGAA     933

ATGTTATGTG AGTTATATAA AGATCAGTGG AAAAAAAAAA AAAAAAAAAA AA
AAAAAAAA    993

AAGCGGCCGC

1003

(2) INFORMATION FOR SEQ ID NO:2:

(i) SEQUENCE CHARACTERISTICS:
         (A) LENGTH: 272 amino
acids
         (B) TYPE: amino acid
         (D) TOPOLOGY: linear (ii) MOLECULE TYPE: protein (xi) SEQUENCE DESCRIPTION:
SEQ ID NO:2:

Met His Leu Leu Leu Val Gln Leu Leu Val Le
u Leu Pro Leu Gly Lys
  1               5
                    10
                      15

Ala Asp Leu Cys Val Asp Gly Cys Gln Ser Gl
n Gly Ser Leu Ser Phe
```

```
            20
            25
            30
Pro Leu Leu Glu Arg Gly Arg Arg Asp Leu Hi
s Val Ala Asn His Glu
     35
     40
     45
Glu Ala Glu Asp Lys Pro Asp Leu Phe Val Al
a Val Pro His Leu Met
    50
    55
    60
Gly Thr Ser Leu Ala Gly Glu Gly Gln Arg Gl
n Arg Gly Lys Met Leu
 65
 70
 75
 80
Ser Arg Leu Gly Arg Phe Trp Lys Lys Pro Gl
u Thr Glu Phe Tyr Pro
            85
            90
            95
Pro Arg Asp Val Glu Ser Asp His Val Ser Se
r Gly Met Gln Ala Val
        100
        105
        110
Thr Gln Pro Ala Asp Gly Arg Lys Val Glu Ar
g Ser Pro Leu Gln Glu
      115
      120
      125
Glu Ala Lys Arg Phe Trp His Arg Phe Met Ph
e Arg Lys Gly Pro Ala
     130
     135
     140
Phe Gln Gly Val Ile Leu Pro Ile Lys Ser Hi
s Glu Val His Trp Glu
145                      1
50                       1
55                       1
60
Thr Cys Arg Thr Val Pro Phe Asn Gln Thr Il
e Ala His Glu Asp Cys
              165
              170
              175
Gln Lys Val Val Val Gln Asn Asn Leu Cys Ph
e Gly Lys Cys Ser Ser
          180
          185
          190
Ile Arg Phe Pro Gly Glu Gly Ala Asp Ala Hi
s Ser Phe Cys Ser His
        195
        200
        205
Cys Ser Pro Thr Lys Phe Thr Thr Val His Le
u Arg Leu Asn Cys Thr
     210
     215
     220
Ser Pro Thr Pro Val Val Lys Met Val Met Gl
n Val Glu Glu Cys Gln
```

```
225                 2
30                  2
35                  2
40

Cys Met Val Lys Thr Glu Arg Gly Glu Glu Ar
g Leu Leu Leu Ala Gly
            245
                250
                    255

Ser Gln Gly Ser Phe Ile Pro Gly Leu Pro Al
a Ser Lys Thr Asn Pro
            260
                265
                    270
```

(2) INFORMATION FOR SEQ ID NO:3:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TGCCCTTCAM YCAGAMYATT GYMCATGAAR ACTGT

35

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CAGAACAAYC TKTGCTTTGG TAAATGCA

28

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TGYTCCCAYT GCTYGCCSWC CAAATT

26

(2) INFORMATION FOR SEQ ID NO:6:

(i) SEQUENCE CHARACTERISTICS:
        (A) LENGTH: 15 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ
ID NO:6:

CATGGGCAGC TCGAG

15

(2) INFORMATION FOR SEQ ID NO:7:

(i) SEQUENCE CHARACTERISTICS:
          (A) LENGTH: 34 base
pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ
ID NO:7:

CTGCAGGCGA GCCTGAATTC CTCGAGCCAT CATG

34

(2) INFORMATION FOR SEQ ID NO:8:

(i) SEQUENCE CHARACTERISTICS:
          (A) LENGTH: 68 base
pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ
ID NO:8:

CGAGGTTAAA AAACGTCTAG GCCCCCCGAA CCACGGGGAC GTGGTTTTCC TT
TGAAAAAC        60

ACGATTGC

68
```

What is claimed is:

1. An isolated DNA molecule comprising a DNA sequence starting at nucleotide #58, 109, 112, 115, 118, 121, 124, 127, 130, 178, 313, 316, 319, 322, 325, 328 or 541 of SEQ ID NO: 1 and ending at nucleotide #780 or 873 of SEQ ID NO: 1.

2. An isolated DNA molecule, comprising a DNA sequence fully complementary to the DNA sequence of claim 1.

3. A vector comprising the DNA sequence of claim 1 in operative association with an expression control sequence therefore.

4. An isolated host cell transformed with the vector of claim 3.

5. An isolated DNA molecule comprising a DNA sequence encoding amino acids starting at amino acid #1, 18 to 25, 41, 85 to 91, or 162 of SEQ ID NO:2 and ending at amino acid #241 or 272 of SEQ ID NO:2.

6. An isolated DNA molecule, comprising a DNA sequence fully complementary to the DNA sequence of claim 5.

7. A vector comprising the DNA sequence of claim 5 in operative association with an expression control sequence therefore.

8. An isolated host cell transformed with the vector of claim 7.

9. An isolated DNA molecule comprising a DNA sequence starting at nucleotide #325 of SEQ ID NO: 1 and ending at nucleotide #873 of SEQ ID NO: 1.

10. An isolated DNA molecule, comprising a DNA sequence fully complementary to the DNA sequence of claim 9.

11. A vector comprising the DNA sequence of claim 9 in operative association with an expression control sequence therefore.

12. An isolated host cell transformed with the vector of claim 11.

13. An isolated DNA molecule comprising a DNA sequence encoding amino acids starting at amino acid #90 of SEQ ID NO: 2 and ending at amino acid #272 of SEQ ID NO: 2.

14. An isolated DNA molecule, comprising a DNA sequence fully complementary to the DNA sequence of claim 13.

15. A vector comprising the DNA sequence of claim 13 in operative association with an expression control sequence therefore.

16. An isolated host cell transformed with the vector of claim 15.

* * * * *

UNITED STATES PATENT AND TRADEMARK OFFICE
CERTIFICATE OF CORRECTION

PATENT NO.    : 5,935,852
DATED         : August 10, 1999
INVENTOR(S)   : Follettie & DeRobertis It is certified that error appears in the above-identified patent and that said Letters Patent is hereby corrected as shown below:

<u>Title page,</u>
Item [73], after the word "Mass." insert the words -- The Regents of the University of California, Oakland, CA --.

Signed and Sealed this

Ninth Day of September, 2003

JAMES E. ROGAN
*Director of the United States Patent and Trademark Office*